United States Patent
Seo et al.

(10) Patent No.: US 10,495,633 B2
(45) Date of Patent: Dec. 3, 2019

(54) METHOD FOR DETECTING DETECTION OBJECT IN SAMPLE, AND DETECTION KIT USING SAME

(71) Applicant: NANOENTEK, INC., Seoul (KR)

(72) Inventors: Joon Seok Seo, Yongin-si (KR); Kyu Hwan Shim, Seoul (KR)

(73) Assignee: NANOENTEK, INC., Seoul (KR)

(*) Notice: Subject to any disclaimer, the term of this patent is extended or adjusted under 35 U.S.C. 154(b) by 185 days.

(21) Appl. No.: 15/313,382

(22) PCT Filed: May 22, 2015

(86) PCT No.: PCT/KR2015/005191
§ 371 (c)(1),
(2) Date: Nov. 22, 2016

(87) PCT Pub. No.: WO2015/178729
PCT Pub. Date: Nov. 26, 2015

(65) Prior Publication Data
US 2017/0184572 A1    Jun. 29, 2017

(30) Foreign Application Priority Data
May 23, 2014 (KR) .................. 10-2014-0062143

(51) Int. Cl.
| C12Q 1/68 | (2018.01) |
| G01N 33/53 | (2006.01) |
| G01N 33/533 | (2006.01) |
| G01N 33/74 | (2006.01) |
| G01N 33/543 | (2006.01) |

(52) U.S. Cl.
CPC ............ *G01N 33/533* (2013.01); *C12Q 1/68* (2013.01); *G01N 33/53* (2013.01); *G01N 33/54306* (2013.01); *G01N 33/74* (2013.01)

(58) Field of Classification Search
CPC ........... C12Q 1/68; G01N 33/53; C07H 21/00
See application file for complete search history.

(56) References Cited

U.S. PATENT DOCUMENTS

| 4,650,770 A * | 3/1987 | Liu .................. G01N 33/542 436/523 |
| 6,541,213 B1 * | 4/2003 | Weigl ................ B01F 5/0403 210/198.2 |
| 2009/0214420 A1 * | 8/2009 | Brown ............... C07K 16/40 424/1.49 |
| 2015/0024513 A1 | 1/2015 | Chung et al. |

FOREIGN PATENT DOCUMENTS

| JP | 52-106794 A | 9/1977 |
| JP | 2012-177683 A | 9/2012 |
| KR | 10-2003-0055483 A | 7/2003 |
| KR | 10-2013-0034078 A | 4/2013 |
| KR | 10-2013-0095530 A | 8/2013 |
| KR | 10-1353930 B1 | 1/2014 |
| WO | WO-93/17335 A1 | 9/1993 |
| WO | WO-2008/053973 A1 | 5/2008 |
| WO | WO-2010/009438 A1 | 1/2010 |
| WO | WO-2011/005357 A2 | 1/2011 |
| WO | WO-2013/072509 A1 | 5/2013 |

OTHER PUBLICATIONS

Extended European Search Report dated Oct. 4, 2017 for European Patent Application No. 15795399.3, Seo et al., "Novel method for detecting detection object in sample, and detection kit using same," filed May 22, 2015 (7 pages).
Notice of Allowance dated Aug. 10, 2015 for Korean Patent Application No. 10-2014-0062143, Seo et al., "A novel method for detecting an analyte and kits using it," filed May 23, 2014 (3 pages).
Office Action dated Sep. 7, 2017 for Japanese Patent Application No. 2016-569433, Seo et al., "Novel method for detecting detection object in sample, and detection kit using same," filed May 22, 2015 (6 pages).
International Search Report dated Jul. 8, 2015, for Seo et al., International Application No. PCT/KR2015/05191, filed May 22, 2015 (14 pages).
Office Action dated Jan. 2, 2019 for Chinese Patent Application No. 201580027380.0, Seo et al., "Novel method for detecting detection object in sample, and detection kit using same," filed May 22, 2015 (11 pages).

* cited by examiner

*Primary Examiner* — Ethan C Whisenant
(74) *Attorney, Agent, or Firm* — Clark & Elbing LLP; Susan M. Michaud

(57) ABSTRACT

The present invention relates to a novel method for detecting a detection object in a sample, and a detection device using the same. The detecting method of the present invention uses a "bridge composite" in which gold nanoparticles and an antibody specific to a detection object are coupled in order to induce a sufficient coupling reaction between the antibody and the detection object, thereby improving reactivity. Accordingly, since excellent resolution is provided, the method of the present invention has advantages of enabling accurate concentration measurement of a detection object in a sample, and amplifying a measurement signal. In addition, the method of the present invention can effectively detect small molecules such as hormones, vitamins, etc. having a small molecular weight.

15 Claims, 6 Drawing Sheets

METHOD FOR DETECTING DETECTION OBJECT IN SAMPLE, AND DETECTION KIT USING SAME

TECHNICAL FIELD

This application claims priority to and the benefit of Korean Patent Application No. 10-2014-0062143 filed in the Korean Intellectual Property Office on 23 May 2014, the entire contents of which are incorporated herein by reference.

The present invention relates to a novel method for detecting an analyte in a sample and to a detection kit using the same.

BACKGROUND ART

Testosterone, which is a male hormone responsible for secondary sex characteristics, belongs to the androgen group of steroid hormones, and is secreted primarily from sex glands. With respect to the male menopause, testosterone is associated with: (1) reduced sex desire, erectile capacity, and frequency; (2) reduced intellectual activity, cognitive functions, and spatial skills, and changes in mood, such as fatigue, feeling low, and anxiety; (3) sleep disorder; (4) reduced body fat mass, in association with reduced muscle mass and muscle strength; (5) increased visceral fat; (6) reduced body hair and skin diseases; and (7) osteopenia and increased fracture risk due to reduced bone density.

The quantity of testosterone existing mainly in the blood is analyzed for diagnosis. The increased testosterone is associated with androgen resistance, ovarian cancer, testicular cancer, congenital adrenal hyperplasia, or precocious puberty, and the reduced testosterone is associated with chronic diseases, abnormal pituitary gland, delayed puberty, abnormal testicles, or noncancerous tumors composed of pituitary gland cells overproducing prolactin.

The testosterone existing in the body is not in a free state: most of the testosterone is in a state of being bound to protein. That is, only about 2-3% of testosterone is in a free state, and 44-65% of testosterone exists in a state of being bound to sex hormone binding globulin (SHBG) and 33-54% of testosterone exists in a state of being bound to albumin. Due to these facts, the testosterone in the blood is difficult to detect.

In order to remove proteins binding to testosterone, it is necessary to use an acid solution causing protein denaturation or 2-methoxyestradiol (2-ME), which is a hormone having a similar structure to testosterone. In some cases, the reaction conditions and the reaction reagents can be controlled in order to obtain a free state of testosterone obtaining sufficient signals.

When a hormone, such as testosterone (molecular weight: 288.42), is applied to a conventional detection method, the small molecular weight thereof makes it impossible to use a sandwich assay.

The detection method of the present invention uses a competitive assay, and thus, the present invention is to establish a method capable of detecting small molecules, such as testosterone, more accurately, by using gold nanoparticles as a medium to amplify measurement signals with response sensitivity increased compared with a conventional assay using competitive reaction.

Throughout the entire specification, many papers and patent documents are referenced and their citations are represented. The disclosure of the cited papers and patent documents are entirely incorporated by reference into the present specification, and the level of the technical field within which the present invention falls and the details of the present invention are explained more clearly.

DETAILED DESCRIPTION OF THE INVENTION

Technical Problem

The present inventors endeavored to develop a novel method for detecting an analyte in a sample. As a result, the present inventors developed a method wherein, if an analyte is present in a sample, the analyte in the sample binds to a "bridge complex", so that the "bridge complex", to which the analyte is bound, and a "competitor carrier complex" generating a signal do not bind to a binding equivalent on a support, and as a result, the signal is not generated on the support, and thus, the analyte in the sample can be accurately detected. Unlike a conventional liquid flow assay, which was applied to analysis immediately after a non-target material binding to an analyte was separated using acidification or an analog of the analyte, the method of the present invention is derived such that the analyte in the sample, separated from the binding protein, is brought in contact with a particle to which a binder (e.g., antibody) specific to the analyte is bound, and thus a complex of the analyte, the binder, and the particle is allowed to apply to flow analysis. Through the above procedure, a sufficient reaction of the analyte and the binder was induced to complete a loading sample in a state suitable for the detection method of the present invention, so that it was confirmed that more precise qualitative and quantitative analysis was possible. In addition, the present invention can minimize the influence by external factors to improve data safety since a separate washing procedure is not required, and can provide a precise resolution compared with a conventional method, thereby accurately measuring the concentration of the analyte in the sample and amplifying a measurement signal.

Accordingly, an aspect of the present invention is to provide a novel method for detecting an analyte in a sample.

Another aspect of the present invention is to provide a novel kit for detecting an analyte in a sample.

Other purposes and advantages of the present invention will become more obvious with the following detailed description of the invention, claims, and drawings.

Technical Solution

In accordance with an aspect of the present invention, there is provided a method for detecting an analyte in a sample, the method comprising:

(a) bringing a sample into contact with (i) a competitor carrier complex comprising a binding equivalent with the same binding characteristics as an analyte and being capable of generating a signal, and (ii) a bridge complex comprising a binder capable of specifically binding to the analyte, wherein, if the analyte is present in the sample, the analyte in the sample binds to the bridge complex;

(b) bringing the product in step (a) into contact with a binding equivalent, with the same binding characteristics as an analyte, bound to a test zone on a support, wherein, if the analyte is present in the sample, the bridge complex, to which the analyte in the sample is bound, does not bind to the binding equivalent on the support and thus does not generate a signal on the support, and if the analyte is absent in the sample, the bridge complex binds to the binding equivalent on the support and the competitor carrier complex binds to the bridge complex to generate a signal on the support; and (c) measuring the intensity of the signal generated from the competitor carrier complex in the product of step (b).

The present inventors endeavored to develop a novel method for detecting an analyte in a sample. As a result, the present inventors developed a method wherein, if an analyte is present in a sample, the analyte in the sample binds to a "bridge complex", so that the "bridge complex", to which the analyte is bound, and a "competitor carrier complex" generating a signal do not bind to a binding equivalent on a support, and as a result, the signal is not generated on the support, and thus, the analyte in the sample can be accurately detected. Unlike a conventional liquid flow assay, which was applied to analysis immediately after a non-target material binding to an analyte was separated using acidification or an analog of the analyte, the method of the present invention is derived such that the analyte in the sample, separated from the binding protein, is brought in contact with a particle to which a binder (e.g., antibody) specific to the analyte is bound, and thus a complex of the analyte, the binder, and the particle is allowed to apply to flow analysis. Through the above procedure, a sufficient reaction of the analyte and the binder was induced to complete a loading sample in a state suitable for the detection method of the present invention, so that it was confirmed that more precise qualitative and quantitative analysis was possible. In addition, the present invention can minimize the influence by external factors to improve data safety since a separate washing procedure is not required, and can provide a precise resolution compared with a conventional method, thereby accurately measuring the concentration of the analyte in the sample and amplifying a measurement signal.

The detection method of the present invention is to detect an analyte present in an analyte sample using a competitive reaction, and in consideration of a conventional competitive assay in which: (i) when an analyte is allowed to bind to an antibody immobilized to a support in a reaction (internal reaction) during fluid flow, the reaction time between the analyte in the sample and the antibody is not enough, and thus accurate quantitative analysis is difficult; and (ii) when the analyte is allowed to react with the antibody in a reaction (external reaction) prior to the fluid flow, a detection signal is not generated, or when the antibody is allowed to bind to a bead to proceed the external reaction, a washing procedure for removing the antibody bound to the bead is separately required at the time of signal measurement, the present inventors endeavored to develop a method for detecting an analyte in a sample in order to solve the problems of the conventional competitive assay, and as a result, the method of the present invention was designed.

According to an embodiment of the present invention, in order to separate a protein (e.g., globulin or albumin) bound to testosterone as the analyte, a competitor hormone (e.g., 2-methoxyestradiol) is used, but in addition to this, various known methods for separating the analyte from a non-target material may be employed.

According to the method of the present invention, (1) the reactivity can be improved by inducing a sufficient binding reaction between an antibody and an analyte using a "bridge complex" in which an antibody specific to the analyte is coupled with a gold nanoparticle; (2) the analyte can be separated at a precise concentration range due to excellent resolution, and thus an accurate concentration of the analyte in the sample can be measured; and (3) small molecules having a small molecular weight, such as hormones and vitamins, can be effectively detected.

As used herein, the term "sample" refers to a material including an analyte, and examples of the sample include organic materials derived from all mammals and artificially synthesized organic molecules, but are not limited thereto. Examples of the sample include biological samples (such as a virus-, bacterium-, cell- or tissue-derived extract, a lysate or purified material, blood, blood plasma, serum, lymph, bone marrow fluid, saliva, eyeball fluid, spermatic fluid, a brain extract, spinal fluid, joint fluid, thymic fluid, ascitic fluid, and amniotic fluid), contaminants, toxins, toxic chemicals, forensic materials, and similar materials. The organic molecule refers to a molecule that has a covalent bond between carbon, nitrogen, oxygen, and/or sulfur atoms. The organic molecule may be selected from between small-sized molecules, such as carbon monoxide, and large-sized complicated molecules, such as a polymer.

As used herein, the term "binding equivalent" refers to any biological compound having the same binding characteristics as an analyte. In the present invention, the analyte and the binding equivalent each may be a protein, a peptide, a carbohydrate, a lipid, a nucleic acid, or a compound. The analyte and the binding equivalent each include various biochemical hormones and analogs thereof, and examples thereof include testosterone, thyroid stimulating hormone (TSH), human growth hormone, progesterone, human chorionic gonadotropin (hCG), and analog hormones thereof. According to an embodiment of the present invention, the binding equivalent is testosterone-3-carboxymethyl oxime-BSA.

According to the present invention, the analyte and the binding equivalent each include biochemical hormones and biochemical hormones bound to proteins, and more specifically, testosterone, testosterone bound to sex hormone binding globulin (SHBG), or testosterone bound to albumin. The method of the present invention can be widely used in detecting small molecules, such as vitamin D, as well as testosterone.

As used herein, the term "competitor carrier complex" refers to a complex comprising a binding equivalent and a particle or bead. A binding equivalent having the same binding characteristics as an analyte is coupled with the particle or bead. The particle or bead can generate a signal, and examples of the particle or bead include a nanoparticle, a microparticle, a nanobead, or a microbead. The particle or bead may have a diameter of 200 nm to 1000 nm. According to the present invention, the particle or bead may have a diameter of 200 nm to 500 nm. According to the present invention, the competitor carrier complex functions as a complex in which the binding equivalent and the bead are coupled with each other, and more specifically, the binding equivalent coupled with the bead of the competitor carrier complex may bind to the antibody which binds to the bridge complex.

As used herein, the term "binder" refers to a material specifically binding to an analyte, and the binder includes a protein, a peptide, a carbohydrate, a lipid, a nucleic acid, and a compound, which are specific to the analyte. Examples of the binder include an antibody, a modified antibody, an antibody analog, an aptide, a receptor, streptavidin, avidin, neutravidin, an aptamer, lectin, a substrate, DNA, RNA, a lipid, and a viral protein. According to the present invention, the binder is an antibody.

As used herein, the term "bridge complex" refers to a complex comprising a binder and a particle or bead. A binder specifically binding to the analyte is coupled with the particle or bead, and the binder of the bridge complex may bind to an analyte in the sample or a binding equivalent. The particle or bead includes a nanoparticle, a microparticle, a nanobead, or a microbead. The particle or bead may have a diameter of 20 nm to 80 nm, and according to the present invention, the particle or bead may have a diameter of 40 nm to 50 nm.

According to the present invention, the bridge complex is a complex of "a gold nanoparticle and an antibody specific to an analyte". Meanwhile, the bridge complex may include a plurality of binders per one particle.

Hereinafter, the method for detecting an analyte in a sample according to the present invention will be described in detail.

Step (a): Contact of Sample, Competitor Carrier Complex, and Bridge Complex

First, a sample is brought into contact with (i) a competitor carrier complex having a binding equivalent with the same binding characteristics as an analyte and (ii) a bridge complex having a binder specifically binding to the analyte.

If the analyte is present in the sample, the analyte in the sample binds to the bridge complex.

The analyte in the sample binding to the bridge complex can react with the competitor carrier complex competitively and simultaneously, or may react selectively and sequentially. For example, (i) when the sample, the competitor carrier complex, and the bridge complex are brought into simultaneous contact with one another, the bridge complex binds to the analyte in the sample competitively with respect to the competitor carrier complex, and (ii) when the sample, the competitor carrier complex, and the bridge complex are brought into selective and sequential contact with one another, the bridge complex binds to the analyte (sample) or the binding equivalent (competitor carrier complex) and a competitive reaction hardly occurs unlike in the simultaneous contact.

According to the present invention, after the binding complex of the analyte in the sample and the bridge complex is formed, the competitor carrier complex may bind to a residual binder of the bridge complex. For example, the binding complex of the analyte and the bridge complex is formed by the reaction of the sample and the bridge complex, and then, when the binding complex is applied to a detection kit of the present invention, the binding complex binds to the binding equivalent on the test zone, and then the competitor carrier complex binds to a non-binding antibody of the bridge complex.

According to the present invention, the competitor carrier complex includes a colored particle as a particle, and a signal is directly generated from the colored particle. For example, the colored particle is a fluorescent molecule particle, colored metal particle, a colored liposome, a black carbon particle, a colored polymer particle, a phosphorescent molecule particle, or a dye molecule particle.

According to the present invention, the particle or bead of the competitor carrier complex further comprises a detectable signal generation label, and the signal may be generated from the signal generation label. The term "signal" refers to a detectable parameter, and examples thereof include a flow of optical, electric, or magnetic parameters, fluorescence emission, infrared radiation, ultraviolet radiation, chemiluminescence, light reflection, and an absorption degree of the signal. The label generating a detectable signal includes a chemical material (e.g., biotin), an enzymatic (e.g., alkaline phosphatase, β-galactosidase, horse radish peroxidase, and cytochrome P450), a radioactive material (e.g., $C^{14}$, $I^{125}$, $P^{32}$, and $S^{35}$), a fluorescent (e.g., fluorescein), a luminescent, a chemiluminescent, and a fluorescence resonance energy transfer (FRET), but is not limited thereto. Various labels and labeling methods are described in Ed Harlow and David Lane, *Using Antibodies: A Laboratory Manual*, Cold Spring Harbor Laboratory Press, 1999.

As for the label, each different fluorescent signal may be observed depending on the wavelength of emission. The label may contain various known fluorescent materials, and examples thereof may include fluorescein and derivatives thereof, rhodamine and derivatives thereof, phycoerythrin, lucifer yellow, B-phycoerythrin, 9-acridineisothiocyanate, lucifer yellow VS, 4-acetamido-4'-isothio-cyanatostilbene-2,2'-disulfonic acid, 7-diethylamino-3-(4'-isothiocyanato-phenyl)-4-methylcoumarin, succinimidyl-pyrenebutyrate, 4-acetamido-4'-isothiocyanatostilbene-2,2'-disulfonic acid derivative, LCm-Red 640, LCm-Red 705, PC5, Cy5, Cy5.5, lissamine, isothiocyanate, erythrosine isothiocyanate, diethylenetriamine pentaacetate, 1-dimethylaminonaphthyl-5-sulfonate, 1-anilino-8-naphthalene sulfonate, 2-p-touidinyl-6-naphthalene sulfonate, 3-phenyl-7-isocyanatocoumarin, 9-isothiocyanatoacridine, acridine orange, N-(p-(2-benzoxazolyl)phenyl)maleimide, benzoxadiazole, stilbene, and pyrene, but are not limited thereto.

In the method of the present invention, when the analyte is a biochemical hormone binding to protein, step (a) may comprise the following sub-steps:

(a-1) bringing the sample, which is treated with a displacement agent for displacing the biochemical hormone from the biochemical hormone binding to protein, into contact with the bridge complex; and (a-2) bringing the product of step (a-1) into contact with the competitor carrier complex.

The displacement agent is a reagent for displacing the biochemical hormone and the protein, and an acid, an alkali, a heavy metal, an organic solvent, a competitor hormone, or the like may be used therefor. According to the present invention, the displacement agent is a competitor hormone (e.g., 2-methoxyestradiol), and the competitive hormone acts competitively with respect to the biochemical hormone (e.g., testosterone) to separate the protein (sex hormone binding globulin or albumin) binding to the biochemical hormone.

Meanwhile, the competitor carrier complex may be located at the upstream of the test zone on the support before step (a) is conducted. In this case, the sample passes through the test zone, to which the binding equivalent is bound, together with the competitor carrier complex.

According to the present invention, the sample containing the analyte may be located on the support sequentially in a fluid-flow manner, the supporting including: (i) a "sample zone" into which the sample is introduced; (ii) a "competitor carrier complex zone" in which the sample is brought into contact with the competitor carrier complex; and (iii) a "test zone" to which the bridge complex and/or the competitor carrier complex can bind, wherein the three zones may sequentially located on the support in a fluid flow manner. For example, when the analyte is a biochemical hormone binding to protein, step (a) is performed such that the sample, which is treated with a displacement agent for displacing the biochemical hormone from the biochemical hormone binding to protein, is brought into contact with the bridge complex to obtain a sample/bridge complex reaction product, and then the sample/bridge complex reaction product is applied to the sample zone; and step (b) is performed such that the sample/bridge complex reaction product and the competitor carrier complex are moved to the test zone through fluid flow to be brought in contact with the binding equivalent bound to the test zone.

Step (b): Contact of Binding Equivalent of Test Zone and Product in Step (a)

The product in step (a) is brought into contact with a binding equivalent, with the same binding characteristics as an analyte, bound to a test zone on a support.

Here, if the analyte is present in the sample, the bridge complex, to which the analyte in the sample is bound, does not bind to the binding equivalent on the support and thus does not generate a signal on the support; and if the analyte is absent in the sample, the bridge complex binds to the binding equivalent on the support and the competitor carrier complex binds to the bridge complex to generate a signal on the support.

According to the present invention, the binding equivalent is bound to the support, and the binding equivalent is present on a surface of a substrate of one reaction container, on which reaction products continuously flow. The reaction container is a microchip having a microchannel.

As used herein, the term "support" may be used as having the same meaning as a "solid substrate", "solid support", or "solid phase", and means a non-liquid material. The support may have a microchannel formed therein, and, for example, the support may exist as small-diameter beads flowing/ attached in a membrane, a portion of a capillary tube, or a microchannel. Such a type of known material includes polystyrene, polypropylene, glass, metal, and a hydrocarbon polymer, such as a gel. The support may be present in the form of a dipstick, a microtiter plate, a particle (e.g., a bead), an affinity column, and an immunoblot membrane (e.g., a polyvinylidene fluoride membrane) (see, U.S. Pat. Nos. 5,143,825, 5,374,530, 4,908,305, and 5,498,551).

Step (c): Signal Measurement

The intensity of the signal generated from the competitor carrier complex in the product of step (b) is measured using a signal measurement device.

According to the method of the present invention, the signal emitted from the label contained in the competitor carrier complex is measured as a fluorescent signal. Therefore, the presence of an analyte can be checked by measuring the fluorescent signal in the test zone, and the sample passing through the test zone can be quantitatively analyzed through a series of procedures. According to the present invention, the quantitative analysis of an analyte is conducted by the method described in Korean Registration No. 10-1353930.

According to the present invention, the microchannel on the support comprises a test zone and a reference zone. The binding equivalent may be bound to a surface of the test zone, and an animal-derived peptide or a detection antibody selected as a material bindable to the peptide may be bound to the reference zone. In some cases, the binding equivalent or a detection antibody specific to the analyte may be bound to the test zone.

As used herein, the term "test zone" is a section included in the microchannel of the support for fluid flow analysis, and the binding equivalent with the same binding characteristics as the analyte is bound to the surface of the test zone.

As used herein, the term "reference zone" is a section included in the microchannel of the support, to which an animal-derived peptide or a detection antibody selected as a material bindable to the peptide may be bound. In some cases, the binding equivalent or the antibody specific to the analyte is bound to the surface of the reference zone, and thus the binding equivalent or the analyte passing through the test zone may be bound to the reference zone.

The binding equivalent or antibody may be attached to a solid substrate by physical adsorption or chemical attachment. The physical adsorption is conducted by a reaction between an antibody or antigen in an appropriate buffer and a solid-phase material. The buffer may be a phosphate buffer, a tris-hydrochloride buffer, or a carbonate buffer. The reaction is conducted by mixing and maintaining the buffer at 4-37° C., especially at room temperature, for a predetermined period of time. The chemical attachment may be conducted by using a carbodiimide method in peptide attachment methods. Another chemical method is a method conducted using a divalent cross-linking reagent, such as glutaraldehyde or cyanuric chloride (cf. "Peptide Synthetic Method", Maruzen, 1975 or "Enzyme Immunoassay Method", Kyoritsu Shuppan, "Protein Nucleic acid Enzyme", special issue No. 31, 1987).

According to the present invention, the sample is applied to the microchip, and the sample is brought into contact with the test zone and the reference zone through the flow formed in the microchannel.

Detailed description of the method for measuring a signal is disclosed in Korean Registration No. 10-1353930.

In accordance with another aspect of the present invention, there is provided a kit for detecting an analyte in a sample, the kit comprising:

(a) a support having a microchannel in which a sample is accommodated and a reaction occurs;

(b) a competitor carrier complex zone, (i) which is formed in one site of the microchannel, and (ii) to which a competitor carrier complex is bound, the competitor carrier complex having a binding equivalent with the same binding characteristics as an analyte and being capable of generating a signal; and (c) a test zone, (i) which is formed in one site of the microchannel and (ii) to which a binding equivalent is bound, the binding equivalent having the same binding characteristics as the analyte and being capable of binding to a bridge complex having a binder specifically binding to an analyte, wherein, if an analyte is present in the sample, the analyte in the sample binds to the bridge complex, and the bridge complex, to which the analyte in the sample is bound, does not bind to the binding equivalent on the support and thus does not generate a signal on the support, and if an analyte is absent in the sample, the bridge complex binds to the binding equivalent on the support and the competitor carrier complex binds to the bridge complex to generate a signal on the support.

Since the detection device of the present invention is for the foregoing method for detecting an analyte in a sample of the present invention, descriptions of overlapping contents therebetween are omitted to avoid excessive complexity of the specification.

Respective components of the device of the present invention will be described in detail.

Component (a): Support Having Microchannel

The detection device of the present invention comprises a support in which a sample is accommodated and a reaction occurs. A microchannel for accommodating an analyte sample therein is provided in the support, and the microchannel may have various depths.

The microchip, in which an analyte sample can be accommodated, may include at least one microchannel, and a binding equivalent and a detection antibody for detecting different objects of detection may be bound to the microchannel. The microchannel may comprise a sample zone, a reaction start zone, a competitor carrier complex zone, a test zone, a reference zone, and a reaction end zone. For example, the respective zones may be located in the order of the sample zone, the reaction start zone, the competitor carrier complex zone, the test zone, the reference zone, and the reaction end zone.

The microchannel may comprise a sample inlet into which the sample may be injected. When the sample flows into the microchannel through the inlet, the sample binds or does not bind to the binding equivalent located in the test zone while passing through the microchannel.

Meanwhile, for the detection of the analyte, a labelling reaction of an analyte sample using a fluorescent material or a specific reaction of an analyte sample using an antigen-antibody reaction may occur in the microchannel. That is, subsequently, by using a protein antigen-antibody specific reaction or the like, only a desired object can be selectively confirmed through various detection units. The labeled analyte sample passes through the microchannel, and here, one sectional surface of the microchannel is exposed to an optical sensor, which is then used to detect a fluorescence signal.

Component (b): Competitor Carrier Complex Zone

In the detection device of the present invention, the competitor carrier complex zone is designed such that: the competitor carrier complex zone is formed at one site in the microchannel; and a competitor carrier complex is bound to the competitor carrier complex zone, the competitor carrier complex having a binding equivalent with the same binding characteristics as the analyte and being capable of generating a signal.

According to the present invention, the competitor carrier complex zone is located at the upstream side of the test zone on the support.

Component (c): Test Zone

In the antigen detection device of the present invention, the test zone is designed such that the test zone is formed at one site in the microchannel; and a binding equivalent is bound to the test zone, the binding equivalent having the same binding characteristics as the analyte and being capable of binding to the bridge complex having a binder specifically binding to the analyte.

Here, if an analyte is present in the sample, the analyte in the sample binds to the bridge complex, and the bridge complex, to which the analyte in the sample is bound, does not bind to the binding equivalent on the support and thus does not generate a signal on the support; and if an analyte is absent in the sample, the bridge complex binds to the binding equivalent on the support and the competitor carrier complex binds to the bridge complex to generate a signal on the support.

According to the present invention, the support included in the detection device of the present invention includes (i) a sample zone, (ii) a competitor carrier complex zone, and (iii) a test zone, the three zones being sequentially located on the support in a fluid-flow manner.

The detection device of the present invention may further comprise a reference zone, wherein the reference zone is formed at one side in the microchannel and a reference material specifically binding to the analyte or the binding equivalent is bound to a surface of the reference zone.

According to the present invention, the device may further comprise, as a reference material, a detection antibody, to which a label generating a detectable signal binds and which specifically binds to the analyte or the binding equivalent.

According to the present invention, the device may further comprise a measurement unit for measuring a signal generated from the label, or the device may further comprise an analysis unit for calculating the ratio of the intensities of the signals measured in the test zone and the reference zone.

The method and device of the present invention may be used in various manners. For example, for the detection of a hormone as a small molecule, the analyte in the sample can be within a precise concentration range by effectively displacing the non-target protein and the biding hormone in the sample in a free hormone state to provide excellent resolution.

Advantageous Effects

Features and advantages of the present invention are summarized as follows:

(a) The present invention relates to a novel method for detecting an analyte in a sample and a detection device using the same.

(b) The detection method of the present invention can improve reactivity by inducing a sufficient binding reaction between an antibody and an analyte using a "bridge complex" in which an antibody specific to the analyte is bound to a gold nanoparticle.

(c) Therefore, the present invention can provide an excellent resolution, thereby accurately measuring the concentration of the analyte in the sample and amplifying a measurement signal.

(d) Furthermore, the method of the present invention can effectively detect small molecules with a small molecular weight, such as a hormone and a vitamin.

BRIEF DESCRIPTION OF THE DRAWINGS

FIG. 2 illustrates the measurement of the displacement degree according to the concentration of the testosterone.

FIG. 3 illustrates the correlation according to the detection method. In FIG. 3a, a correlation of 0.7414 is shown, and In FIG. 3b, the correlation is high, but a separate washing procedure is required. In the present invention, a washing procedure is not required, and a high correlation is also shown.

ABBREVIATION

Anti-Testosterone F.B.: Anti-Testosterone Fluorescence bead

Testo-3CMO:BSA-Ⓑ: Testosterone-3-carboxymethyloxime-bovine serum albumin-Biotin

Anti-Testosterone-Ⓑ: Anti-Testosterone-Biotin

2-ME: 2-methoxyestradiol

MODE FOR CARRYING OUT THE INVENTION

Figure 1:
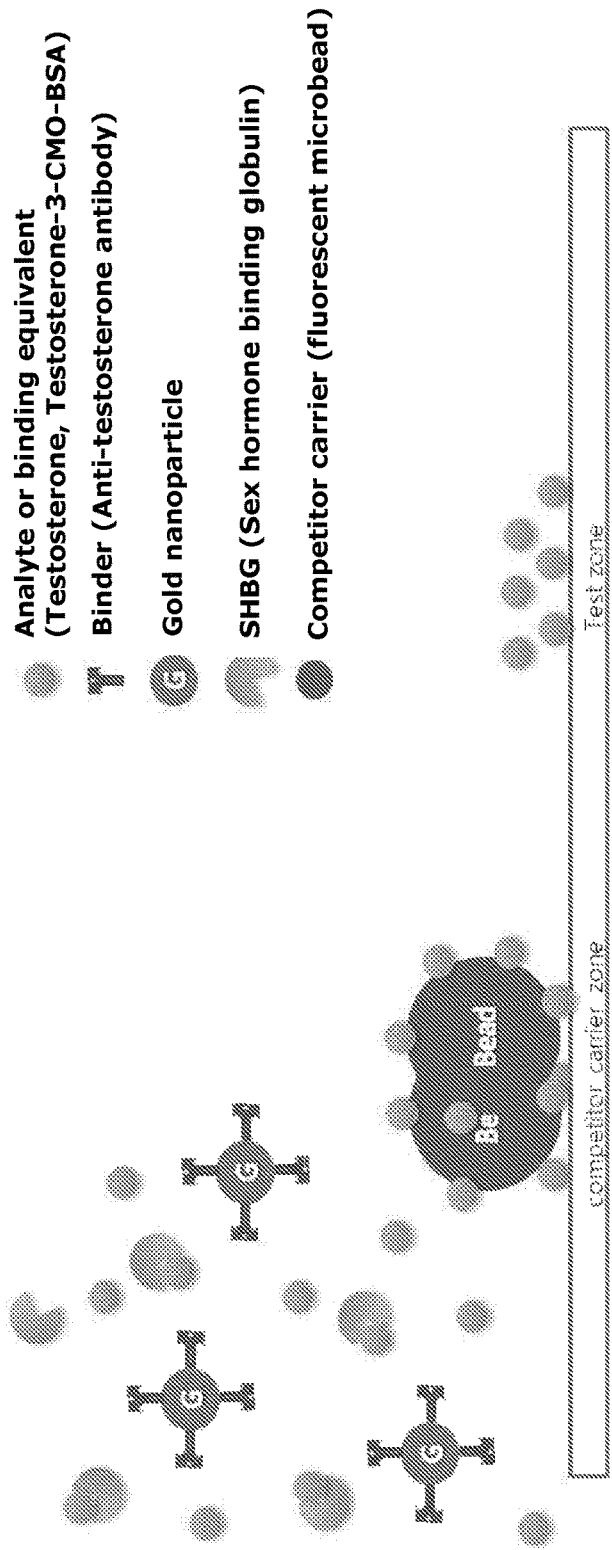
FIG. 1 schematically illustrates a detection method of the present invention.
Figure 2A:
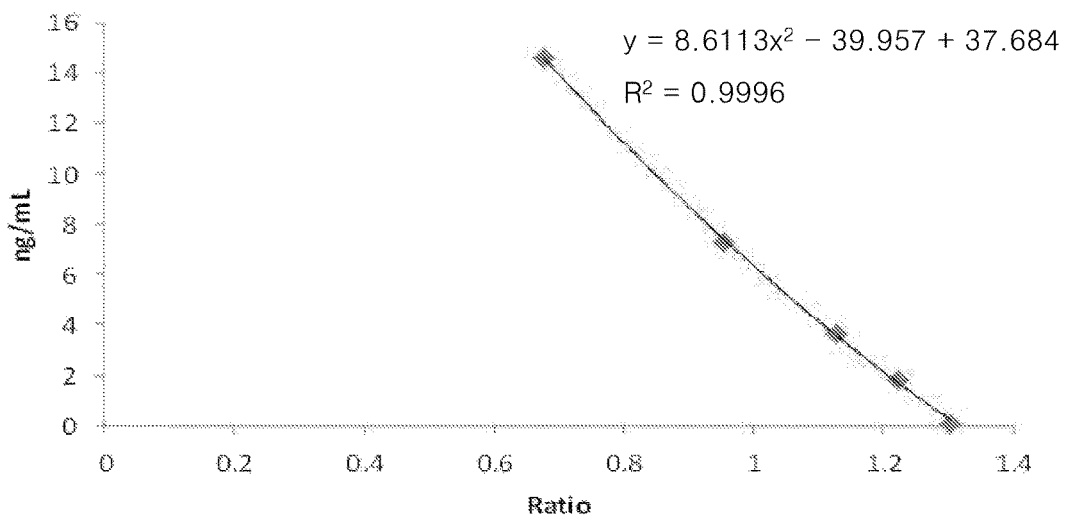
FIG. 2a shows a calibration curve according to conventional detection methods 1 and 2 without using a gold nanoparticle.
Figure 2B:
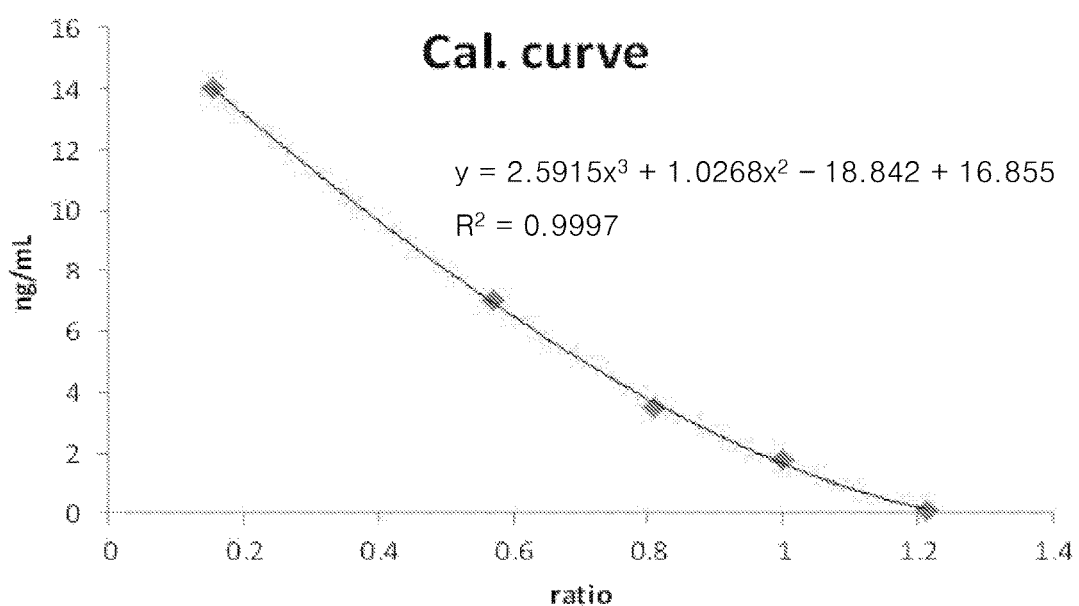
FIG. 2b shows a calibration curve according to the method of the present invention using a gold nanoparticle. The horizontal line represents the ratio of the test zone signal (test intensity) to the reference zone signal (signal intensity), and the vertical line represents the concentration of testosterone. It was verified that the range of the average value of the measured signal and the displacement degree (Dis. %) were greater when using the method of the present invention compared with the conventional methods.
Figure 3A:
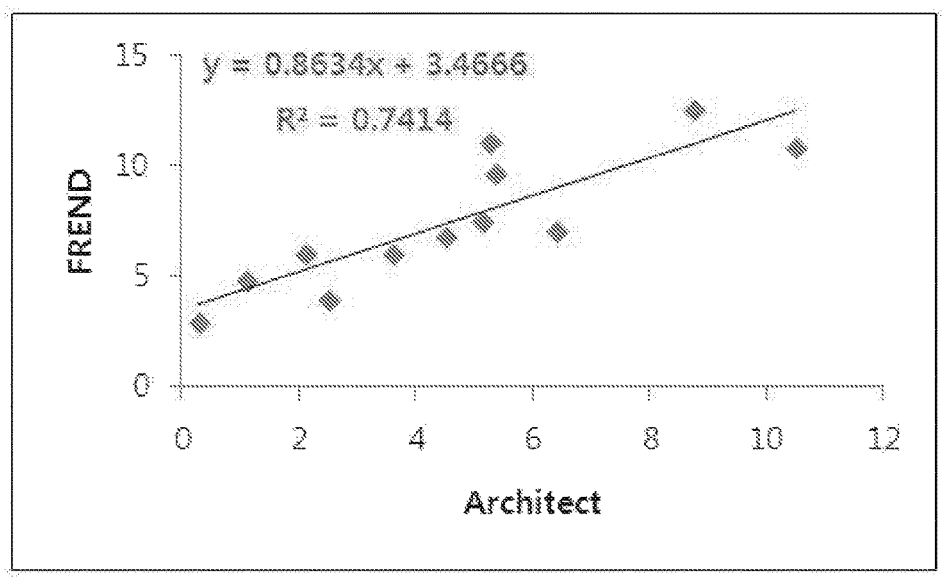
FIG. 3a illustrates the correlation according to conventional detection methods 1 and 2.
Figure 3B:
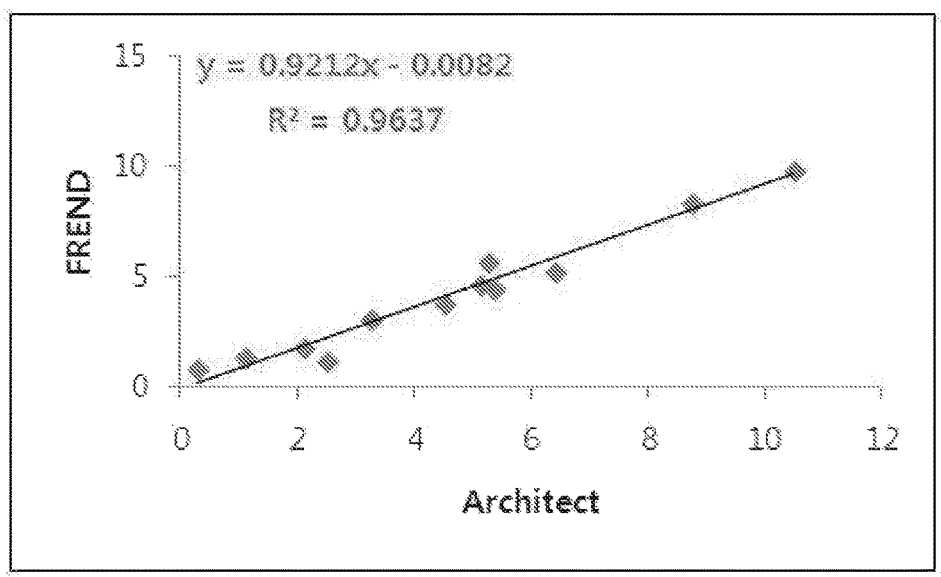
FIG. 3b illustrates the correlation according to conventional detection method 3.
Figure 3C:
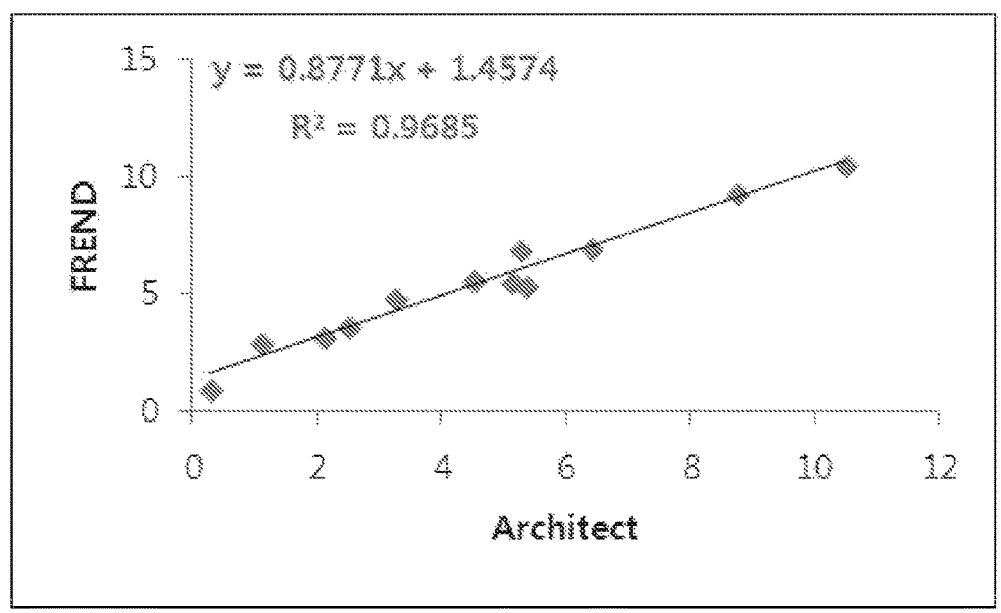
FIG. 3c illustrates the correlation according to the method of the present invention.
Figure 4:
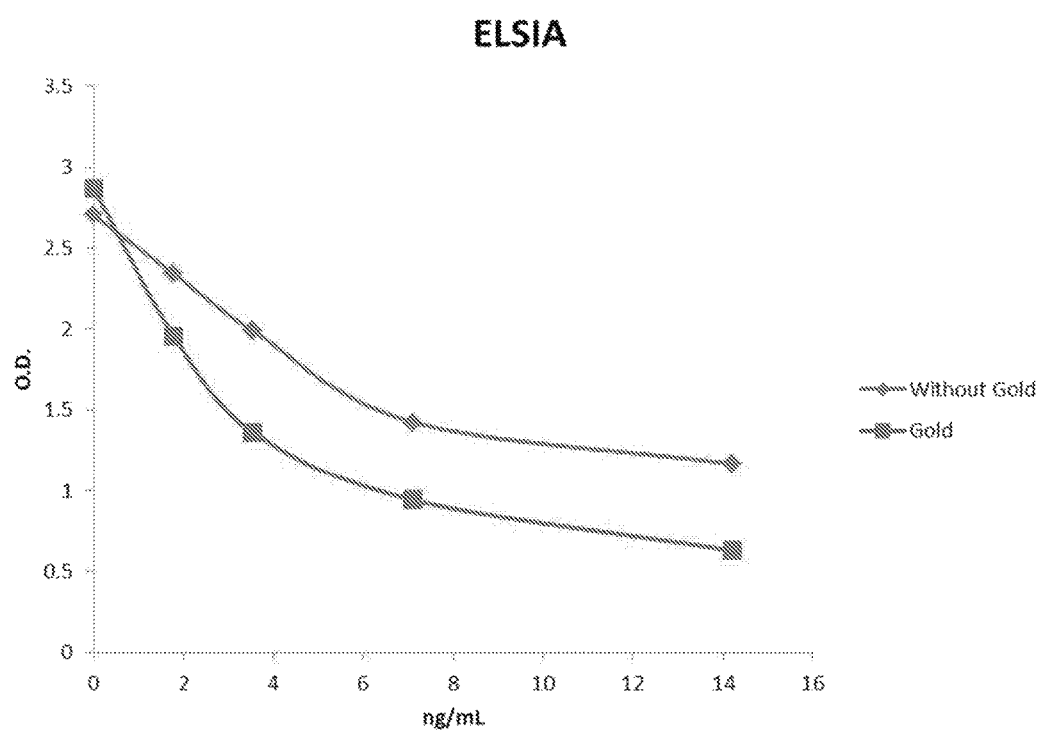
FIG. 4 illustrates ELISA results for resolution comparison between with and without a medium including a gold nanoparticle. It was verified that the use of the gold nanoparticle showed a broad O.D. measurement value range.

Hereinafter, the present invention will be described in detail with reference to examples. These examples are only for illustrating the present invention more specifically, and it will be apparent to those skilled in the art that the scope of the present invention is not limited by these examples.

EXAMPLES

Example 1: Antibody Coupling with Gold Nanoparticle

A gold nanoparticle with a diameter of about 40 nm and an antibody (anti-testosterone or anti-vitamin D) were mixed at a predetermined ratio in a test tube, followed by a reaction at room temperature for 1 hour. The antibody was added to reach a final concentration of 5 µg/mL.

Thereafter, 10% bovine serum albumin (BSA) in a phosphate (PB) buffer was added to the reaction mixture to reach 1.1%, followed by a reaction at room temperature for 1 hour.

The reaction product was centrifuged at 10,000 rpm for 15 minutes, and then the supernatant was removed.

A storage buffer (0.1% casein in 2 mM borate) was put in the tube, from which the supernatant was removed, followed by suspension. The centrifugation and re-suspension processes were repeated two additional times, followed by storage at 4° C.

Example 2: Antigen Coupling with Fluorescent Microparticle

A fluorescent microparticle (or microbead) with a diameter of about 500 nm was activated using 1-(3-dimethylaminopropyl)-3-ethylcarbodiimide/N-hydroxysuccinimide (EDC/NHS). Then, the activated fluorescent microparticle and an antigen (testosterone-3-carboxymethyloxime-bovine serum albumin (testosterone-3-CMO-BSA) or vitamin D) were mixed at a predetermined ratio in a test tube (2% fluorescent microparticle 100 µl and antigen 250 µg), followed by reaction at room temperature for 2 hours.

Thereafter, 10% BSA in distilled water was added to the reaction mixture to reach a final concentration of 1%, followed by reaction at room temperature for 1 hour.

1 M glycine was added to the reaction product to reach a final concentration of 50 mM, followed by reaction at room temperature for 30 minutes. Then, the centrifugation and re-suspension processes in example 1 were repeated, followed by storage at 4° C.

Example 3: Biotinylation of Testosterone 3CMO BSA

Testosterone 3CMO BSA and biotin were mixed at a predetermined ratio, followed by reaction at room temperature for 1 hour (20 mol biotin/1 mol antibody).

Thereafter, dialysis was conducted in PBS in order to remove an unreacted material. In order to sufficiently remove the unreacted biotin during the dialysis procedure, new PBS replacement was conducted about three or four times. The concentration of the biotin-removed antibody was checked using a UV spectrometer, and then stored at 4° C.

Example 4: Chip Preparation

Biotinylated-testosterone or biotinylated-vitamin D was dotted on a lower substrate of avidin-coupled chip, followed by reaction at room temperature for 1 hour.

Then, the chip was washed with a washing buffer, followed by sufficient drying at 37° C., and then a sample buffer (2-methoxyestradiol, 2-ME) and a testosterone-fluorescent microparticle were dotted on the lower substrate, followed by sufficient drying at 37° C. The prepared lower and upper substrates were coupled with each other, and then stored in a dryer before use.

Example 5: Testosterone Measurement

2-ME and the gold nanoparticle solution in example 1 were mixed with the blood, followed by reaction at room temperature for 5 minutes. 35 µl of the mixed reaction product was dropped on the chip in example 4, and when the mixed reaction product passed through all the reaction routes of the chip, a fluorescent signal was measured using FREND (NANOENTEK, Korea).

In the comparison of the displacement degree of testosterone between the method of the present invention and the conventional detection method, it was verified that the average value range of the signal and the displacement degree (Dis. %) were broader in the detection method of the present invention, and thus it was confirmed that the method of the present invention can provide high resolution.

TABLE 1

Numerical values in conventional reactions 1 and 2

| | Testosterone concentration (ng/mL) | FREND measurement value (Aver.) | Displacement degree (%) |
|---|---|---|---|
| 1 | 0.1 | 1.304 | 100 |
| 2 | 1.75 | 1.224 | 93.87 |
| 3 | 3.5 | 1.127 | 86.43 |
| 4 | 7 | 0.954 | 73.16 |
| 5 | 14 | 0.679 | 52.07 |

TABLE 2

Numerical values in present method

| | Testosterone concentration (ng/mL) | FREND measurement value (Aver.) | Displacement degree (%) |
|---|---|---|---|
| 1 | 0.1 | 1.214 | 100 |
| 2 | 1.75 | 1.000 | 82.37 |
| 3 | 3.5 | 0.810 | 66.72 |
| 4 | 7 | 0.569 | 46.87 |
| 5 | 14 | 0.153 | 12.60 |

Example 6: Vitamin D Measurement

A gold nanoparticle solution containing a releasing reagent was mixed with the blood, followed by reaction at 49° C. for 10 minutes. 35 µl of the mixed reaction product was dropped on the chip in example 4, and then when the mixed reaction product passed through all the reaction routes of the chip, a fluorescent signal was measured using FREND.

Like in example 5, it was verified that the average value range of the signal and the displacement degree (Dis. %) were broader in the detection method of the present invention.

TABLE 3

Numerical values in conventional reactions 1 and 2

| — | Vitamin D concentration (ng/mL) | FREND measurement value (Aver.) |
|---|---|---|
| 1 | 0 | 2.10 |
| 2 | 21 | 2.01 |
| 3 | 46 | 1.81 |
| 4 | 77 | 1.73 |
| 5 | 145 | 1.61 |

TABLE 4

Numerical values in present invention

| — | Vitamin D concentration (ng/mL) | FREND measurement value (Aver.) |
|---|---|---|
| 1 | 0 | 0.6 |
| 2 | 21 | 0.48 |
| 3 | 46 | 0.34 |
| 4 | 77 | 0.25 |
| 5 | 145 | 0.14 |

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A method for detecting an analyte in a sample, the method comprising:
    (a) bringing a sample into contact with (i) a competitor carrier complex comprising a binding equivalent with the same binding characteristics as an analyte and being capable of generating a signal, and (ii) a bridge complex comprising a binder capable of specifically binding to the analyte, wherein, if the analyte is present in the sample, the analyte in the sample binds to the bridge complex;
    (b) bringing the product of step (a) into contact with a binding equivalent, with the same binding characteristics as an analyte, bound to a test zone on a support, wherein, if the analyte is present in the sample, the bridge complex, to which the analyte in the sample is bound, does not bind to the binding equivalent on the support and thus does not generate a signal on the support, and if the analyte is absent in the sample, the bridge complex binds to the binding equivalent on the support and the competitor carrier complex binds to the bridge complex to generate a signal on the support; and
    (c) measuring the intensity of the signal generated from the competitor carrier complex in the product of step (b).

2. The method of claim 1, wherein the analyte and the binding equivalent each are a protein, a peptide, a carbohydrate, a lipid, a nucleic acid, or a compound.

3. The method of claim 2, wherein the analyte and the binding equivalent each are a biochemical hormone.

4. The method of claim 3, wherein the analyte and the binding equivalent each are a biochemical hormone binding to protein.

5. The method of claim 4, wherein the analyte is a biochemical hormone binding to protein, and wherein step (a) comprises the following sub-steps of:
    (a-1) bringing the sample, which is treated with a displacement agent for displacing the biochemical hormone from the biochemical hormone binding to protein, into contact with the bridge complex; and
    (a-2) bringing the product of step (a-1) into contact with the competitor carrier complex.

6. The method of claim 1, wherein the competitor carrier complex comprises a particle or bead.

7. The method of claim 6, wherein the particle is a colored particle and the signal is directly generated from the colored particle.

8. The method of claim 6, wherein the particle further comprises a signal generation label.

9. The method of claim 1, wherein the binder of the bridge complex is an antibody, a modified antibody, an antibody analog, an aptide, a receptor, streptavidin, avidin, neutravidin, an aptamer, lectin, a substrate, DNA, RNA, a lipid, or a viral protein.

10. The method of claim 1, wherein the bridge complex comprises a particle or bead.

11. The method of claim 1, wherein the bridge complex comprises a plurality of binders per one particle.

12. The method of claim 1, wherein in step (a), the sample is first brought in contact with the bridge complex, and then brought in contact with the competitor carrier complex.

13. The method of claim 1, wherein the competitor carrier complex is located at the upstream of the test zone on the support before step (a) is conducted.

14. The method of claim 1, wherein the support comprises (i) a sample zone, (ii) a competitor carrier complex zone, and (iii) a test zone, the three zones being sequentially located on the support in a fluid-flow manner.

15. The method of claim 14, wherein the analyte is a biochemical hormone binding to protein,
    wherein step (a) is performed such that the sample, which is treated with a displacement agent for displacing the biochemical hormone from the biochemical hormone binding to protein, is brought into contact with the bridge complex to obtain a sample/bridge complex reaction product, and then the sample/bridge complex reaction product is applied to the sample zone, and
    wherein step (b) is performed such that the sample/bridge complex reaction product and the competitor carrier complex are moved to the test zone through fluid flow to be brought in contact with the binding equivalent bound to the test zone.

* * * * *